US010875972B2

(12) United States Patent
Grünewald et al.

(10) Patent No.: US 10,875,972 B2
(45) Date of Patent: Dec. 29, 2020

(54) METHOD FOR THE PRODUCTION OF SUPERABSORBERS

(71) Applicant: BASF SE, Ludwigshafen (DE)

(72) Inventors: Gerald Grünewald, Ludwigshafen (DE); Ruediger Funk, Ludwigshafen (DE); Matthias Weismantel, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/304,714

(22) PCT Filed: May 23, 2017

(86) PCT No.: PCT/EP2017/062327
§ 371 (c)(1),
(2) Date: Nov. 27, 2018

(87) PCT Pub. No.: WO2017/207330
PCT Pub. Date: Dec. 7, 2017

(65) Prior Publication Data
US 2019/0276608 A1  Sep. 12, 2019

(30) Foreign Application Priority Data

May 31, 2016 (EP) .................... 16172267

(51) Int. Cl.
| | | |
|---|---|---|
| *C08J 3/075* | (2006.01) | |
| *A61L 15/60* | (2006.01) | |
| *B01J 20/26* | (2006.01) | |
| *B01J 20/30* | (2006.01) | |
| *C08F 220/06* | (2006.01) | |
| *C08J 3/12* | (2006.01) | |
| *C08J 3/24* | (2006.01) | |

(52) U.S. Cl.
CPC ............. *C08J 3/075* (2013.01); *A61L 15/60* (2013.01); *B01J 20/261* (2013.01); *B01J 20/267* (2013.01); *B01J 20/30* (2013.01); *B01J 20/3021* (2013.01); *C08F 220/06* (2013.01); *C08J 3/12* (2013.01); *C08J 3/245* (2013.01); *B01J 2220/68* (2013.01); *C08J 2333/02* (2013.01)

(58) Field of Classification Search
CPC ............... B01J 20/3021; B01J 20/267
See application file for complete search history.

(56) References Cited

U.S. PATENT DOCUMENTS

| | | | | |
|---|---|---|---|---|
| 2001/0011123 A1* | 8/2001 | Kakita | ............ | C08J 3/12 |
| | | | | 528/503 |
| 2001/0025093 A1* | 9/2001 | Ishizaki | ............ | C08J 3/12 |
| | | | | 526/210 |
| 2007/0225160 A1* | 9/2007 | Kitano | ............ | C08J 3/203 |
| | | | | 502/402 |
| 2009/0022603 A1 | 1/2009 | Feise et al. | | |
| 2009/0060660 A1 | 3/2009 | Funk et al. | | |
| 2009/0060661 A1 | 3/2009 | Feise et al. | | |
| 2010/0249320 A1 | 9/2010 | Matsumoto et al. | | |
| 2011/0015351 A1* | 1/2011 | Nogi | ............ | B01J 20/26 |
| | | | | 525/385 |
| 2011/0166300 A1* | 7/2011 | Dairoku | ............ | C08F 6/003 |
| | | | | 525/384 |
| 2011/0207906 A1* | 8/2011 | Funk | ............ | C08F 6/008 |
| | | | | 526/317.1 |
| 2012/0016084 A1* | 1/2012 | Dairoku | ............ | C08J 3/12 |
| | | | | 525/115 |
| 2012/0283401 A1* | 11/2012 | Funk | ............ | A61L 15/24 |
| | | | | 526/181 |
| 2016/0144341 A1* | 5/2016 | Hamilton | ............ | C08F 8/00 |
| | | | | 502/402 |

FOREIGN PATENT DOCUMENTS

| | | | |
|---|---|---|---|
| EP | 1 118 633 A2 | 7/2001 | |
| EP | 1 130 045 A2 | 9/2001 | |
| EP | 2 253 375 A1 | 11/2010 | |
| EP | 2 258 749 A1 | 12/2010 | |
| EP | 2 338 918 A1 | 6/2011 | |
| EP | 2 415 822 A1 | 2/2012 | |
| EP | 2 471 847 A1 | 7/2012 | |
| EP | 2 471 848 A1 | 7/2012 | |
| WO | WO-2007/104657 A2 | 9/2007 | |
| WO | WO-2007/104673 A2 | 9/2007 | |
| WO | WO-2007/104676 A1 | 9/2007 | |
| WO | WO-2010040466 A1 * | 4/2010 | ............ C08F 2/10 |
| WO | WO-2012/119969 A1 | 9/2012 | |

OTHER PUBLICATIONS

Buchholz, et al., eds., "Modern Superabsorbent Polymer Technology," Wiley-VCH, NY, NY (1998), pp. 71-103.
International Search Report for Patent Application No. PCT/EP2017/062327, dated Sep. 5, 2017.

* cited by examiner

*Primary Examiner* — Mark S Kaucher
(74) *Attorney, Agent, or Firm* — Marshall, Gerstein & Borun LLP

(57) ABSTRACT

A process for producing superabsorbents, comprising polymerization, drying, crushing, pneumatic conveying, comminuting and classifying, wherein the gas temperature at the end of the pneumatic conveying is from 50 to 95° C.

16 Claims, No Drawings

METHOD FOR THE PRODUCTION OF SUPERABSORBERS

CROSS-REFERENCE TO RELATED APPLICATIONS

This is a U.S. national phase of International Application No. PCT/EP2017/062327, filed May 23, 2017, which claims the benefit of Italian Patent Application No. 16172267.3, filed May 31, 2016.

The present invention relates to a process for producing superabsorbents, comprising polymerization, drying, crushing, pneumatic conveying, comminuting and classifying, wherein the gas temperature at the end of the pneumatic conveying is from 50 to 95° C.

Superabsorbents are used to produce diapers, tampons, sanitary napkins and other hygiene articles, but also as water-retaining agents in market gardening. Superabsorbents are also referred to as water-absorbing polymers.

The production of superabsorbents is described in the monograph "Modern Superabsorbent Polymer Technology", F. L. Buchholz and A. T. Graham, Wiley-VCH, 1998, pages 71 to 103.

The properties of the superabsorbents can be adjusted, for example, via the amount of crosslinker used. With increasing amount of crosslinker, the centrifuge retention capacity (CRC) falls and the absorption under a pressure of 21.0 g/cm² (AUL0.3 psi) passes through a maximum.

To improve the performance properties, for example, permeability of the swollen gel bed (SFC) in the diaper and absorption under a pressure of 49.2 g/cm² (AUL0.7 psi), superabsorbent particles are generally surface postcrosslinked. This increases the level of crosslinking of the particle surface, which can at least partly decouple the absorption under a pressure of 49.2 g/cm² (AUL0.7 psi) and the centrifuge retention capacity (CRC). This surface postcrosslinking can be performed in the aqueous gel phase. Preferably, however, dried, ground and sieved polymer particles (base polymer) are surface coated with a surface postcrosslinker and thermally surface postcrosslinked. Crosslinkers suitable for that purpose are compounds which can form covalent bonds to at least two carboxylate groups of the polymer particles.

EP 1 118 633 A2, EP 1 130 045 A2, EP 2 258 749 A1 and WO 2012/119969 A1 disclose processes for producing superabsorbents.

EP 1 118 633 A2 teaches the heating of surfaces in storage and transport of superabsorbents.

EP 1 130 045 A2 teaches cooling between the drying of aqueous polymer gels and the subsequent comminution.

EP 2 258 749 A1 teaches the use of dry gases and smooth pipelines in pneumatic conveying.

WO 2012/119969 A1 teaches pneumatic conveying between comminution and classification.

It was an object of the present invention to provide an improved process for producing superabsorbents, with the particular intention of reducing faults in the classification of the base polymer.

The object was achieved by a process for producing superabsorbents by polymerizing a monomer solution or suspension comprising
a) an ethylenically unsaturated monomer which bears acid groups and is at least partly neutralized,
b) at least one crosslinker,
c) at least one initiator,
d) optionally an ethylenically unsaturated monomer copolymerizable with the monomers mentioned under a) and
e) optionally one or more water-soluble polymers,
comprising the steps of
i) polymerizing the monomer solution or suspension,
ii) optionally comminuting the polymer gel obtained in step i),
iii) drying the polymer gel obtained in step i) or step ii) in an air circulation belt drier with multiple heating zones and at least one cooling zone,
iv) crushing the dried polymer gel obtained in step iii),
v) optionally coarsely comminuting the polymer particles obtained in step iv),
vi) pneumatically conveying the polymer particles obtained in step iv) or step v),
vii) optionally removing incompletely dried polymer particles from the polymer particles obtained in step vi), and further processing the remaining dried polymer particles in step viii), step ix) or step x),
viii) optionally classifying the polymer particles obtained in step vi) or step vii), and sending the coarse fraction to step ix) or step x),
ix) optionally intermediately storing the polymer particles obtained in step vi), step vii) or step viii),
x) comminuting the polymer particles obtained in step vi), step vii), step viii) or step ix),
xi) optionally pneumatically conveying the polymer particles obtained in step x),
xii) classifying the polymer particles obtained in step x) or step xi) and
xiii) optionally surface postcrosslinking the classified polymer particles obtained in step viii) and/or step xii),
wherein the gas temperature at the end of the pneumatic conveying in step vi) is from 50 to 95° C., preferably from 53 to 90° C., more preferably from 56 to 85° C., most preferably from 59 to 80° C.

Pneumatic conveying is described, for example, in WO 2007/104657 A2, WO 2007/104673 A2, WO 2007/104676 A1, EP 2 471 847 A1 and EP 2 471 848 A1.

In a preferred embodiment of the present invention, the polymer particles obtained in step vi) or the polymer particles remaining in step vii) after the removal of the incompletely dried polymer particles are classified in step viii), and the coarse fraction is sent to step ix) or step x).

The dwell time between the end of the drying in step iii) and the end of the pneumatic conveying in step vi) is preferably less than 30 minutes, more preferably less than 20 minutes, most preferably less than 10 minutes.

The dwell time in the pneumatic conveying can be ascertained as the quotient of length of the conveying line in m and the average gas velocity in m/s, where the average gas velocity is the arithmetic average of initial gas velocity and final gas velocity. Dwell time in any intermediate vessels between the end of the drying in step iii) and the pneumatic conveying in step vi) should be added on. The dwell time can be determined more accurately by marking experiments, for example colored polymer particles.

In further preferred embodiments of the present invention, the gas temperatures at the end of the pneumatic conveying in step vi) and the dwell times between the end of the drying in step iii) and the end of the pneumatic conveying in step vi) are, for example, from 50 to 95° C. and less than 30 minutes, or from 50 to 95° C. and less than 20 minutes, or from 50 to 95° C. and less than 10 minutes, or from 53 to 90° C. and less than 30 minutes, or from 53 to 90° C. and less than 20 minutes, or from 53 to 90° C. and less than 10 minutes, or from 56 to 85° C. and less than 30 minutes, or from 56 to 85° C. and less than 20 minutes, or from 56 to 85° C. and less than 10 minutes, or from 59 to 80° C. and less than 30 minutes, or from 59 to 80° C. and less than 20 minutes, or from 59 to 80° C. and less than 10 minutes.

The moisture content of the polymer particles in step x) is preferably from 0.5% to 10% by weight, more preferably from 1% to 6% by weight and most preferably from 1.5% to 4% by weight, the moisture content being ascertained by EDANA recommended test method No. WSP 230.2-05 "Mass Loss Upon Heating".

In further preferred embodiments of the present invention, the gas temperatures at the end of the pneumatic conveying in step vi), the dwell times between the end of the drying in step iii) and the end of the pneumatic conveying in step vi) and the moisture content of the polymer particles in step x) are, for example, from 50 to 95° C., less than 30 minutes and from 0.5% to 10% by weight, or from 50 to 95° C., less than 30 minutes and from 1% to 6% by weight, or from 50 to 95° C., less than 30 minutes and from 1.5% to 4% by weight, or from 50 to 95° C., less than 20 minutes and from 0.5% to 10% by weight, or from 50 to 95° C., less than 20 minutes and from 1% to 6% by weight, or from 50 to 95° C., less than 20 minutes and from 1.5% to 4% by weight, or from 50 to 95° C., less than 10 minutes and from 0.5% to 10% by weight, or from 50 to 95° C., less than 10 minutes and from 1% to 6% by weight, or from 50 to 95° C., less than 10 minutes and from 1.5% to 4% by weight, or from 53 to 90° C., less than 30 minutes and from 0.5% to 10% by weight, or from 53 to 90° C., less than 30 minutes and from 1% to 6% by weight, or from 53 to 90° C., less than 30 minutes and from 1.5% to 4% by weight, or from 53 to 90° C., less than 20 minutes and from 0.5% to 10% by weight, or from 53 to 90° C., less than 20 minutes and from 1% to 6% by weight, or from 53 to 90° C., less than 20 minutes and from 1.5% to 4% by weight, or from 53 to 90° C., less than 10 minutes and from 0.5% to 10% by weight, or from 53 to 90° C., less than 10 minutes and from 1% to 6% by weight, or from 53 to 90° C., less than 10 minutes and from 1.5% to 4% by weight, or from 56 to 85° C., less than 30 minutes and from 0.5% to 10% by weight, or from 56 to 85° C., less than 30 minutes and from 1% to 6% by weight, or from 56 to 85° C., less than 30 minutes and from 1.5% to 4% by weight, or from 56 to 85° C., less than 20 minutes and from 0.5% to 10% by weight, or from 56 to 85° C., less than 20 minutes and from 1% to 6% by weight, or from 56 to 85° C., less than 20 minutes and from 1.5% to 4% by weight, or from 56 to 85° C., less than 10 minutes and from 0.5% to 10% by weight, or from 56 to 85° C., less than 10 minutes and from 1% to 6% by weight, or from 56 to 85° C., less than 10 minutes and from 1.5% to 4% by weight, or from 59 to 80° C., less than 30 minutes and from 0.5% to 10% by weight, or from 59 to 80° C., less than 30 minutes and from 1% to 6% by weight, or from 59 to 80° C., less than 30 minutes and from 1.5% to 4% by weight, or from 59 to 80° C., less than 20 minutes and from 0.5% to 10% by weight, or from 59 to 80° C., less than 20 minutes and from 1% to 6% by weight, or from 59 to 80° C., less than 20 minutes and from 1.5% to 4% by weight, or from 59 to 80° C., less than 10 minutes and from 0.5% to 10% by weight, or from 59 to 80° C., less than 10 minutes and from 1% to 6% by weight, or from 59 to 80° C., less than 10 minutes and from 1.5% to 4% by weight.

In a particularly preferred embodiment of the present invention, the cooling output of the at least one cooling zone in step iii) is used to control the gas temperature at the end of the pneumatic conveying in step vi).

The present invention is based on the finding that the gas temperature at the end of the pneumatic conveying has a crucial influence on fault-free operation of the subsequent classification. This temperature can be readily adjusted via the cooling output at the end of the air circulation belt drier used to dry the polymer gel.

The dried polymer gel is crushed in step iv) preferably by means of a spiked roll or a cross-blade comminutor. A cross-blade comminutor comprises a shaft on which a multitude of bars are accommodated. As well as the bars disposed on the shaft, the cross-blade comminutor comprises a multitude of fixedly mounted bars that mesh into spaces between the bars disposed on the shaft. The dried polymer gel introduced into the cross-blade comminutor falls onto the fixedly mounted bars and remains at rest thereon. The bars that rotate with the shaft crush the dried polymer gel.

The polymer particles are comminuted in step x) preferably by means of a multistage roll mill. Suitable roll mills are described, for example, in the monograph "Modern Superabsorbent Polymer Technology", F. L. Buchholz and A. T. Graham, Wiley-VCH, 1998, pages 93 to 95.

The polymer particles are classified in step viii) and/or step xii) preferably by means of a tumbler sieving machine. Suitable tumbler sieving machines are described, for example, in EP 0 855 232 A2 and WO 2006/0574816 A1.

The polymer particles obtained in step iv) are preferably coarsely comminuted in step v) by means of a roll crusher. A roll crusher consists of two counter-rotating rolls, optionally fitted with teeth or pegs, between which the polymer particles can be crushed. The rolls of the roll crusher have an essentially smooth surface, and so the polymer particles are not ground or pulverized.

The polymer particles obtained in step x) can subsequently be conveyed pneumatically in step xi).

Polymer particles incompletely dried in step vii) are preferably separated from the polymer particles obtained in step vi). The removal of incompletely dried polymer particles is described, for example, in EP 0 948 997 A2 and WO 207/057350 A1.

The polymer particles obtained in step vii) can be classified in step viii).

The polymer particles obtained in step vi), step vii) or step viii) can subsequently be stored intermediately in step ix). The containers or silos suitable for this purpose are not subject to any restriction.

The polymer particles obtained in step viii) and/or step xii) are preferably surface postcrosslinked in step xiii).

The production of the superabsorbents is described in detail hereinafter:

The superabsorbents are produced in step i) by polymerizing a monomer solution or suspension, and are typically water-insoluble.

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 02/055469 A1, WO 03/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 02/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or propoxylated glycerols which have been esterified with acrylic acid or methacrylic acid to give di- or triacrylates, as described, for example, in WO 03/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.25 to 1.5% by weight, more preferably 0.3 to 1.2% by weight and most preferably 0.4 to 0.8% by weight, based in each case on unneutralized monomer a). With rising crosslinker content, centrifuge retention capacity (CRC) falls and the absorption under a pressure of 21.0 $g/cm^2$ passes through a maximum.

Initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

Typically, an aqueous monomer solution is used. The water content of the monomer solution is preferably from 40% to 75% by weight, more preferably from 45% to 70% by weight and most preferably from 50% to 65% by weight. It is also possible to use monomer suspensions, i.e. monomer solutions with solubility-exceeding monomer a), for example sodium acrylate. As the water content rises, the energy expenditure in the subsequent drying rises and, as the water content falls, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors for the polymerization in step i) are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel which has to be comminuted in a further step, step ii), for example in an extruder or kneader.

To improve the drying properties, the comminuted polymer gel obtained by means of a kneader can additionally be extruded in step ii).

The acid groups of the resulting polymer gels have typically been partly neutralized. Neutralization is preferably carried out at the monomer stage. This is typically accomplished by mixing in the neutralizing agent as an aqueous solution or else preferably as a solid. The degree of neutralization is preferably from 25 to 85 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

The polymer gel is then dried with an air circulation belt drier in step iii) until the residual moisture content is preferably 0.5 to 10% by weight, more preferably 1 to 6% by weight and most preferably 1.5 to 4% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the polymer gel before the drying is preferably from 25% and 90% by weight, more preferably from 35% to 70% by weight, most preferably from 40% to 60% by weight. Subsequently, the dried polymer gel is crushed in step iv) and optionally coarsely comminuted in step v).

Thereafter, the dried polymer gel is conveyed pneumatically in step vi), comminuted in step x) and classified in step xii), in which case the apparatus used for comminution may typically be single or multistage roll mills, preferably two- or three-stage roll mills, pin mills, hammer mills or vibratory mills.

The average particle size of the polymer particles removed as the product fraction in step xii) is preferably from 150 to 850 μm, more preferably from 250 to 600 μm, very particularly from 300 to 500 μm. The average particle size of the product fraction may be determined by means of EDANA recommended test method No. WSP 220.2-05 "Particle Size Distribution", where the proportions by mass of the screen fractions are plotted in cumulated form and the average particle size is determined graphically. The average particle size here is the value of the mesh size which arises for a cumulative 50% by weight.

The proportion of polymer particles having a particle size of greater than 150 μm is preferably at least 90% by weight, more preferably at least 95% by weight, most preferably at least 98% by weight.

Polymer particles with too small a particle size lower the permeability (SFC). The proportion of excessively small polymer particles ("fines") should therefore be small.

Excessively small polymer particles are therefore typically removed and recycled into the process, preferably before, during or immediately after the polymerization in step i), i.e. prior to the drying of the polymer gel in step iii).

The excessively small polymer particles can be moistened with water and/or aqueous surfactant before or during the recycling.

It is also possible to remove excessively small polymer particles in later process steps, for example after the surface postcrosslinking in step xiii) or another coating step. In this case, the excessively small polymer particles recycled are surface postcrosslinked or coated in another way, for example with fumed silica.

If a kneading reactor is used for polymerization, the excessively small polymer particles are preferably added in step i) during the last third of the polymerization. However, it is also possible to incorporate the excessively small polymer particles into the polymer gel in a step ii) downstream of the polymerization reactor, for example in a kneader or extruder.

If the excessively small polymer particles are added at a very early stage, for example actually to the monomer solution, this lowers the centrifuge retention capacity (CRC) of the resulting polymer particles. However, this can be compensated, for example, by adjusting the amount of crosslinker b) used.

The proportion of polymer particles having a particle size of at most 850 μm is preferably at least 90% by weight, more preferably at least 95% by weight, most preferably at least 98% by weight.

The proportion of polymer particles having a particle size of at most 600 μm is preferably at least 90% by weight, more preferably at least 95% by weight, most preferably at least 98% by weight.

Polymer particles of excessively large particle size lower the free swell rate. The proportion of excessively large polymer particles should therefore likewise be low.

Excessively large polymer particles are therefore typically removed and recycled into the comminution in step x). If the polymer particles are stored intermediately in step ix) prior to the comminution in step x), the excessively large polymer particles removed are preferably recycled into the intermediate storage in step ix).

To further improve the properties, the polymer particles can be surface postcrosslinked in step xiii). Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 03/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyl-2-oxazolidinone, 2-oxazolidinone and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001% to 2% by weight, more preferably 0.02% to 1% by weight and most preferably 0.05% to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process of the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, 0.001% to 1.5% by weight, preferably 0.005% to 1% by weight and more preferably 0.01% to 0.8% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are surface postcrosslinked and dried, and the surface postcrosslinking reaction can take place both before and during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lodige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The surface postcrosslinking is preferably performed in contact driers, more preferably shovel driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany), Holo-Flite® driers (Metso Minerals Industries Inc.; Danville; USA) and Nara Paddle Dryer (NARA Machinery Europe; Frechen; Germany). Moreover, fluidized bed driers may also be used.

The surface postcrosslinking can be effected in the mixer itself, by heating the jacket or blowing in warm air. Equally suitable is a downstream drier, for example a shelf drier, a rotary tube oven or a heatable screw. It is particularly advantageous to effect mixing and thermal surface postcrosslinking in a fluidized bed drier.

Preferred reaction temperatures are in the range of 100 to 250° C., preferably 120 to 220° C., more preferably 130 to 210° C., most preferably 150 to 200° C. The preferred dwell time at this temperature is preferably at least 10 minutes, more preferably at least 20 minutes, most preferably at least 30 minutes, and typically at most 60 minutes.

In a preferred embodiment of the present invention, the polymer particles are cooled after the surface postcrosslinking. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disc Cooler (Hosokawa Micron GmbH; Leingarten; Germany), Holo-Flite® coolers (Metso Minerals Industries Inc.; Danville; USA) and Nara Paddle Cooler (NARA Machinery Europe; Frechen; Germany). Moreover, fluidized bed coolers may also be used.

In the cooler, the polymer particles are cooled to preferably 40 to 90° C., more preferably 45 to 80° C., most preferably 50 to 70° C.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The remoisturizing is preferably performed at 40 to 120° C., more preferably at 50 to 110° C., most preferably at 60 to 100° C. At excessively low temperatures the polymer particles tend to form lumps, and at higher temperatures water already evaporates to a noticeable degree. The amount of water used for remoisturizing is preferably from 1% to 10% by weight, more preferably from 2% to 8% by weight and most preferably from 3% to 5% by weight. The remoisturizing increases the mechanical stability of the polymer particles and reduces their tendency to static charging. The remoisturizing is advantageously performed in the cooler after the thermal surface postcrosslinking.

Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

EXAMPLES

Example 1

By continuously mixing deionized water, 50% by weight sodium hydroxide solution and acrylic acid, an acrylic acid/sodium acrylate solution was prepared such that the degree of neutralization corresponded to 71.3 mol %. The solids content of the monomer solution was 38.8% by weight.

The polyethylenically unsaturated crosslinker used was polyethylene glycol-400 diacrylate (diacrylate proceeding from a polyethylene glycol with a mean molar mass of 400 g/mol). The amount used was 2 kg of crosslinker per t of monomer solution.

To initiate the free-radical polymerization, per t of monomer solution, 1.03 kg of a 0.25% by weight aqueous hydrogen peroxide solution, 3.10 kg of a 15% by weight aqueous sodium peroxodisulfate solution and 1.05 kg of a 1% by weight aqueous ascorbic acid solution were used.

The throughput of the monomer solution was 20 t/h. The reaction solution had a feed temperature of 23.5° C.

The individual components were metered in the following amounts continuously into a List Contikneter continuous kneader reactor with a capacity of 6.3 m³ (LIST AG, Arisdorf, Switzerland):

| | |
|---|---|
| 20 t/h | of monomer solution |
| 40 kg/h | of polyethylene glycol-400 diacrylate |
| 82.6 kg/h | of hydrogen peroxide solution/sodium peroxodisulfate solution |
| 21 kg/h | of ascorbic acid solution |

Between the addition point for the crosslinker and the addition sites for the initiators, the monomer solution was inertized with nitrogen.

After about 50% of the dwell time, polymer particles having a particle size of less than 150 µm that are obtained in the process (1000 kg/h) were metered into the reactor. The dwell time of the reaction mixture in the reactor was 15 minutes.

The polymer gel obtained was applied to an air circulation belt drier. The air circulation belt drier had six heating zones and one cooling zone. On the air circulation belt drier, an air/gas mixture flowed continuously around the polymer gel and dried it. The dwell time in the belt drier was 37 minutes. In the cooling zone of the air circulation belt drier, the polymer gel was cooled down to 100° C.

The dried polymer gel was crushed by means of a cross-blade comminutor and coarsely comminuted by means of a roll crusher. Subsequently, the polymer particles were conveyed pneumatically (pneumatic conveying 1) and the incompletely dried polymer particles were removed. The gas temperature at the end of the pneumatic conveying 1 was 75° C. The dwell time between the end of the drying and the end of the pneumatic conveying 1 was about 2 minutes.

The incompletely dried polymer particles were removed by classifying by means of a vibration sieving machine. Sieves having a mesh size of 8 mm and 12 mm were used. The polymer particles having a particle size of less than 8 mm were stored intermediately in a silo.

Subsequently, the polymer particles were comminuted by means of a two-stage roll mill, conveyed pneumatically (pneumatic conveying 2) and classified by means of a tumbler sieving machine. The water content of the polymer particles was 2.5% by weight.

Polymer particles having a particle size of less than 150 µm were recycled into the reactor. Polymer particles having a particle size of greater than 850 µm were recycled into the silo.

Polymer particles having a particle size in the range from 150 to 850 µm were surface postcrosslinked. The classification ran without faults for several weeks.

The polymer particles were coated with a surface postcrosslinker solution in a Schugi Flexomix® (Hosokawa Micron B.V., Doetinchem, the Netherlands) and then dried in a NARA Paddle Dryer (GMF Gouda, Waddinxveen, the Netherlands) at 190° C. for 45 minutes.

The following amounts were metered into the Schugi Flexomix®:

| | |
|---|---|
| 7.5 t/h | of polymer particles |
| 270.0 kg/h | of surface postcrosslinker solution |

The surface postcrosslinker solution comprised 2.8% by weight of 2-hydroxyethyl-2-oxazolidone, 2.8% by weight of aluminum sulfate, 66.1% by weight of deionized water and 28.3% by weight of isopropanol.

After drying, the surface postcrosslinked base polymer was cooled down to about 60° C. in a NARA Paddle-Cooler (GMF Gouda, Waddinxveen, the Netherlands).

The water-absorbing polymer particles obtained had a centrifuge retention capacity (CRC) of 28.4 g/g.

Example 2

The procedure was as in example 1. The polymer gel was cooled down to 80° C. rather than to 100° C. in the cooling zone of the air circulation belt drier. The gas temperature at the end of the pneumatic conveying 1 was 60° C. rather than 75° C.

The classification ran without faults for several weeks.

Example 3 (Comparative Example)

The procedure was as in example 1. The polymer gel was cooled down to 60° C. rather than to 100° C. in the cooling zone of the air circulation belt drier. The gas temperature at the end of the pneumatic conveying 1 was 40° C. rather than 75° C.

Within a few hours, larger agglomerates within the particle size fraction from 150 to 850 µm and caking on the walls of the tumbler sieving machine were observed.

Example 4 (Comparative Example)

The procedure was as in example 1. The polymer gel was cooled down to 140° C. rather than to 100° C. in the cooling zone of the air circulation belt drier. The gas temperature at the end of the pneumatic conveying 1 was 110° C. rather than 75° C.

Within a few days, individual sieves in the tumbler sieving machine had to be changed owing to damage.

The invention claimed is:

1. A process for producing superabsorbents by polymerizing a monomer solution or suspension comprising
   a) an ethylenically unsaturated monomer which bears an acid group and is at least partly neutralized,
   b) at least one crosslinker,
   c) at least one initiator,
   d) optionally an ethylenically unsaturated monomer copolymerizable with the monomer mentioned under a), and e) optionally one or more water-soluble polymer, comprising i) polymerizing the monomer solution or suspension to provide a polymer gel, ii) optionally comminuting the polymer gel obtained in step i), iii) drying the polymer gel obtained in step i) or step ii) in an air circulation belt drier with multiple heating zones and at least one cooling zone to provide a dry polymer gel, iv) crushing the dried polymer gel obtained in step iii) to provide polymer particles, v) optionally coarsely comminuting the polymer particles obtained in step iv), vi) pneumatically conveying the polymer particles obtained in step iv) or step v), vii) optionally removing incompletely dried polymer particles from the polymer particles obtained in step vi), and further processing the remaining dried polymer particles in step viii), step ix), or step x), viii) optionally classifying the polymer particles obtained in step vi) or step vii), and sending a coarse fraction to step ix) or step x), ix) optionally intermediately storing the polymer particles obtained in step vi), step vii), or step viii), x) comminuting the polymer particles obtained in step vi), step vii), step viii), or step ix), xi) optionally pneumatically conveying the polymer particles obtained in step x), xii) classifying the polymer particles obtained in step x) or step xi), and xiii) optionally surface postcrosslinking the classified polymer particles obtained in step viii) and/or step xii), wherein a gas temperature at the end of the pneumatic conveying in step vi) is from 50 to 95° C., and a cooling output of the at least one cooling zone in step iii) is used to adjust the gas temperature at the end of the pneumatic conveying in step vi).

2. The process according to claim 1, wherein the polymer particles obtained in step vi) or the polymer particles remaining in step vii) after the removal of the incompletely dried polymer particles are classified in step viii), and the coarse fraction is sent to step ix) or step x).

3. The process according to claim 1, wherein the gas temperature at the end of the pneumatic conveying in step vi) is from 59 to 80° C.

4. The process according to claim 1, wherein a dwell time of the polymer particles between the end of the drying in step iii) and the end of the pneumatic conveying in step vi) is less than 30 minutes.

5. The process according to claim 1, wherein a moisture content of the polymer particles in step x) is from 1% to 10% by weight.

6. The process according to claim 1, wherein the dried polymer gel is crushed in step iv) by means of a spiked roller or a cross-blade comminutor.

7. The process according to claim 1, wherein the polymer particles are comminuted in step x) by means of at least one multistage roll mill.

8. The process according to claim 1, wherein the polymer particles are classified in step viii) and/or step xii) by means of at least one tumbler sieving machine.

9. The process according to claim 1, wherein the polymer particles obtained in step iv) are coarsely comminuted in step v) by means of at least one roll crusher.

10. The process according to claim 1, wherein the polymer particles obtained in step x) are conveyed pneumatically in step xi).

11. The process according to claim 1, wherein incompletely dried polymer particles are separated in step vii) from the polymer particles obtained in step vi).

12. The process according to claim 1, wherein the polymer particles obtained in step vii) are classified in step viii).

13. The process according to claim 1, wherein the polymer particles obtained in step viii) and/or step xii) are surface postcrosslinked in step xiii).

14. The process according to claim 1, wherein the polymer particles have a centrifuge retention capacity of at least 15 g/g.

15. The process according to claim 1, wherein the gas temperature at the end of the pneumonic conveying step (vi) is from 53 to 90° C.

16. The process according to claim 1, wherein the gas temperature at the end of the pneumonic conveying step (vi) is from 56 to 85° C.

* * * * *